United States Patent
Feugnet et al.

(10) Patent No.: US 8,920,632 B2
(45) Date of Patent: Dec. 30, 2014

(54) PROCESS FOR CATALYTIC CRACKING WITH A RECYCLE OF AN OLEFINIC CUT REMOVED UPSTREAM OF THE GAS SEPARATION SECTION IN ORDER TO MAXIMIZE PROPYLENE PRODUCTION

(75) Inventors: Frederic Feugnet, Lyons (FR); Romain Roux, Rueil Malmaison (FR)

(73) Assignee: IFP Energies Nouvelles, Rueil-Malmaison Cedex (FR)

(*) Notice: Subject to any disclaimer, the term of this patent is extended or adjusted under 35 U.S.C. 154(b) by 715 days.

(21) Appl. No.: 13/101,221

(22) Filed: May 5, 2011

(65) Prior Publication Data
US 2011/0272326 A1 Nov. 10, 2011

(30) Foreign Application Priority Data
May 6, 2010 (FR) ...................................... 10 01955

(51) Int. Cl.
*C10G 11/00* (2006.01)
*C07C 4/06* (2006.01)
*C10G 11/18* (2006.01)

(52) U.S. Cl.
CPC ............ *C10G 11/18* (2013.01); *C10G 2400/02* (2013.01); *C10G 2300/1088* (2013.01); *C10G 2300/104* (2013.01); *C10G 2300/1011* (2013.01); *C07C 2529/70* (2013.01); *C10G 2300/1044* (2013.01); *C10G 2400/20* (2013.01); *C10G 2300/4081* (2013.01); *C07C 4/06* (2013.01)
USPC .......................................... 208/113; 422/139

(58) Field of Classification Search
USPC ......................................................... 208/113
See application file for complete search history.

(56) References Cited

U.S. PATENT DOCUMENTS

| | | | | |
|---|---|---|---|---|
| 5,009,769 A * | 4/1991 | Goelzer | ........................ | 208/113 |
| 7,008,527 B2 * | 3/2006 | Gauthier et al. | ............... | 208/113 |
| 2008/0035527 A1 * | 2/2008 | Eng et al. | ........................ | 208/113 |
| 2010/0168488 A1 * | 7/2010 | Mehlberg et al. | ............. | 585/324 |
| 2010/0286459 A1 | 11/2010 | Gauthier et al. | | |
| 2011/0272326 A1 * | 11/2011 | Feugnet et al. | ............... | 208/113 |

FOREIGN PATENT DOCUMENTS

| EP | 0 704 517 A2 | 4/1996 |
|---|---|---|
| FR | 2 918 070 A1 | 1/2009 |
| FR | 2 932 495 A1 | 12/2009 |
| WO | WO 2006/104662 A1 | 10/2006 |

OTHER PUBLICATIONS

Micheal J. Tallman et al, Catalytic Routes to Olefins, Apr. 2008, KBR international reference paper 2084, 14 pp.*
Reza Sadeghbeigi, Fluid Catalytic Cracking Handbook: Design, Operation, and Troubleshooting of FCC Facilities,Gulf Professional Publishing, 2000—Technology & Engineering—p. 26.*
Search Report of FR 1001955 (Jan. 5, 2011).

* cited by examiner

*Primary Examiner* — Randy Boyer
*Assistant Examiner* — Juan Valencia
(74) *Attorney, Agent, or Firm* — Miller, White, Zelano & Branigan, P.C.

(57) ABSTRACT

The present invention describes a process for the production of gasoline and for the co-production of propylene employing a catalytic cracking unit having at least one principal reactor operating in riser mode or in downer mode, processing a conventional heavy feed, and in which the principal reactor further processes a feed primarily constituted by olefinic C4, C5 and C6 cuts introduced upstream or as a mixture with said heavy feed, said olefinic feed deriving from the inter-stage of the wet gas compressor, i.e. upstream of the separation section of the catalytic cracking unit.

12 Claims, 1 Drawing Sheet

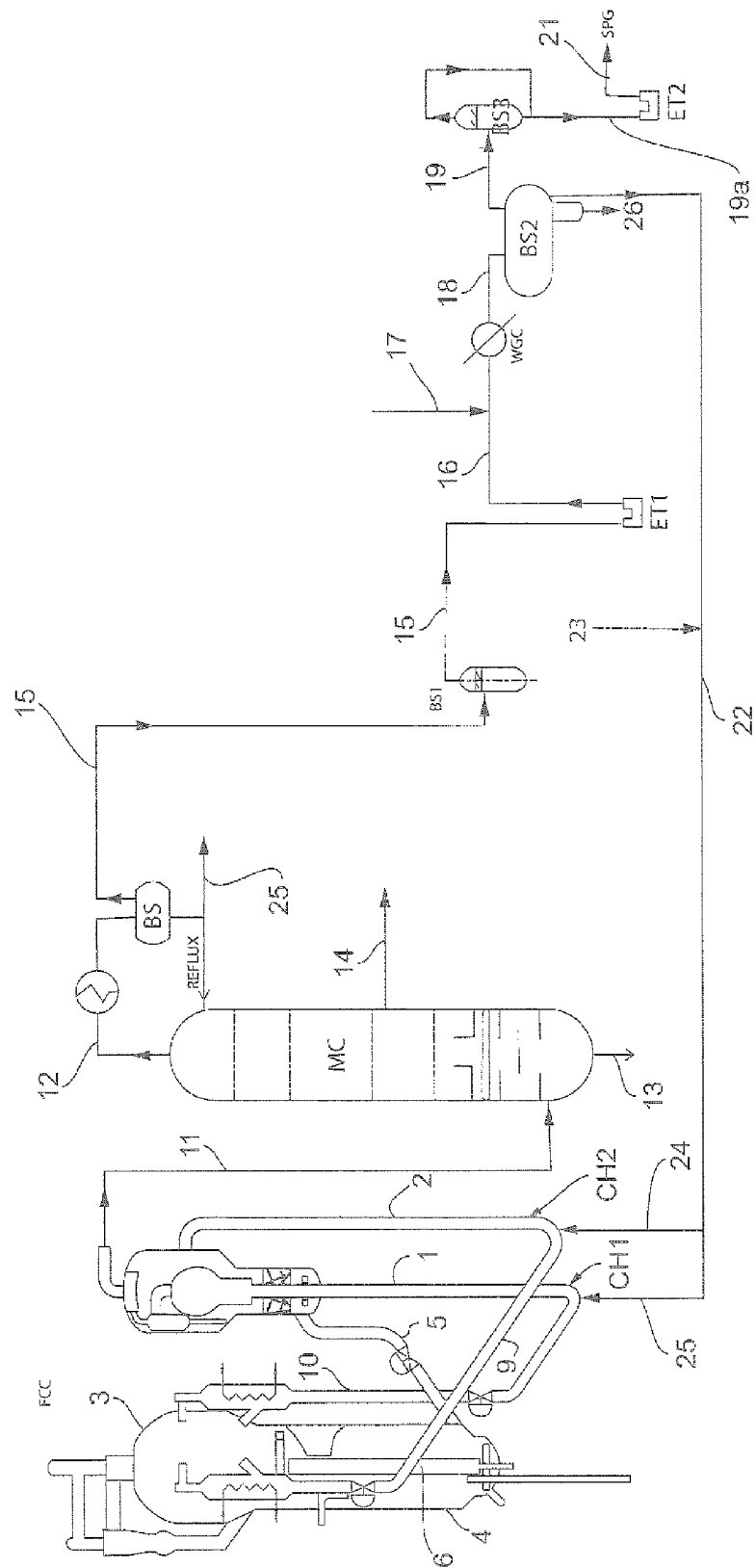

US 8,920,632 B2

PROCESS FOR CATALYTIC CRACKING WITH A RECYCLE OF AN OLEFINIC CUT REMOVED UPSTREAM OF THE GAS SEPARATION SECTION IN ORDER TO MAXIMIZE PROPYLENE PRODUCTION

FIELD OF THE INVENTION

The present invention relates to the field of catalytic cracking of oil cuts, more particularly cuts termed "heavy" cuts, and to the field of the evolution of catalytic cracking towards the co-production of light olefins, in particular propylene.

The principal feed for a FCC unit (abbreviation for fluidized bed catalytic cracking) for heavy cuts is generally constituted by a hydrocarbon or a mixture of hydrocarbons essentially (i.e. at least 80%) containing molecules with a boiling point of more than 340° C. This principal feed also contains limited quantities of metals (Ni+V) in concentrations that are generally less than 50 ppm, preferably less than 20 ppm, and with a hydrogen content which is generally more than 11% by weight, typically in the range 11.5% to 14.5%, and preferably in the range 11.8% to 14% by weight.

The Conradson carbon residue (abbreviated to CCR) of the feed (defined by US standard ASTM D 482) provides an evaluation of the production of coke during catalytic cracking. The Conradson carbon residue of the feed, which determines the coke yield, dictates the specific dimensions of the unit in order to satisfy the thermal balance.

Such heavy cuts can in particular derive from atmospheric distillation, vacuum distillation, the hydroconversion unit, the coking unit, the hydrotreatment or the deasphalting unit, but may also have a biomass type origin, such as vegetable oils or cellulose, for example.

Heavy cuts constituting the principal feed of a catalytic cracking unit are hereinafter termed conventional heavy cuts and may be treated alone or as a mixture.

The principal aim of a catalytic cracking unit of a refinery is the production of bases for gasoline, i.e. cuts with a distillation range in the range 35° C. to 250° C. More and more frequently, this prime objective is being accompanied by a new objective which is the co-production of light olefins, essentially ethylene and propylene.

The production of gasoline is ensured by cracking the heavy feed in the principal reactor, also known as the principal riser in the text below, due to the longilinear shape of that reactor and its riser flow mode. When the flow is downwards in the principal reactor, it is known as a downer.

The co-production of propylene is generally accomplished by adding to the basic catalytic system a zeolite with form selectivity in order to improve the selectivity for LPG (liquid petroleum gas) and gasoline, and also by making the operating conditions for the principal riser more severe, principally by increasing the outlet temperature of the reactor.

In order to obtain higher propylene yields, it is possible to recycle to an additional reactor, generally a secondary riser, a portion of the gasoline cut produced by the catalytic cracking unit, or an equivalent feed such as C6, C7 and C8 oligomers deriving from the refinery.

The present invention describes a novel recycle stream which can maximize the propylene yield.

The skilled person will be aware that a recycle of the catalytic gasoline from FCC to the reaction zone can significantly increase the yield of propylene when suitable operating conditions are used, i.e. a higher temperature at the riser outlet and higher catalyst/feed (denoted C/O) ratios.

The significance of the present invention lies in withdrawing the novel recycle not downstream the separation section but upstream thereof, which means that separation costs are dispensed with and it is possible to benefit from a recycle with properties (chemical composition, especially olefins content) which are as good as if not better (low aromatics content) than those of the prior art gasoline recycle.

The point at which the novel recycled stream is removed is located at the inter-stage of the wet gas compressor. This stream has a composition which is rich in C4, C5, C6 to C8 compounds with good olefinicity (olefins content), and it is practically free of aromatic compounds which, after recycling, tend to principally form coke and thus deleteriously affect the thermal balance of the unit.

EXAMINATION OF THE PRIOR ART

The skilled person will be aware that recycling catalytic gasoline from FCC to the reaction zone can significantly increase the yield of propylene when suitable operating conditions are employed, i.e. a higher temperature at the riser outlet and higher catalyst/feed (C/O) ratios. This recycled gasoline cracking may be carried out in the principal riser of the unit or in a dedicated riser.

The prior art concerning catalytic cracking units with two risers, one of which is conventional for the production of gasoline, the other operating under more severe conditions in order to obtain light olefins, has in particular been described in patent FR 07/04.672.

The present text explores the notions of the principal riser operating on a heavy feed and of a secondary riser operating under severe conditions on a feed partially constituted by the recycle of the gasoline produced in the principal riser.

Further, independent optimization of the operating conditions of the two risers functioning in parallel is described in patent application FR 08/03.384.

The downer configuration is described in patents EP 0 861 310 B1, U.S. Pat. No. 6,664,171 B1 and U.S. Pat. No. 6,656,346 B2.

The arrangement of an internal tube in a riser is described in U.S. Pat. No. 7,008,527 B2.

BRIEF DESCRIPTION OF THE FIGURES

FIG. 1 is a flowsheet for the process of the invention showing withdrawal of the olefinic C4 C5 C6 cut at the inter-stage of the wet gas compressor and its recycling to the principal riser of a FCC unit.

BRIEF DESCRIPTION OF THE INVENTION

The present invention is applicable to FCC units functioning with a single reactor (in riser or downer mode) and to FCC units functioning with two reactors.

In the remainder of the text, the term "principal reactor" 1 will be used to denote the reactor orientated towards conversion of the principal feed, and the term "secondary reactor" 2 will be used to denote the reactor dedicated to the production of propylene by cracking a recycled cut.

In general, when FCC units function with two reactors, a principal and a secondary reactor, these reactors are risers, but a unit which uses two downer reactors are also included in the context of the present invention. It is also possible to consider the case of a unit with one riser and another downer reactor.

Typically, the principal riser functions with a catalyst to feed ratio in the range 4 to 15, preferably in the range 5 to 10, and with riser outlet temperatures (denoted TO) in the range 510° C. to 580° C., preferably in the range 520° C. to 570° C.

The optimum conditions for the production of propylene in the secondary riser are obtained for outlet temperatures of said secondary riser in the range 550° C. to 650° C., preferably in the range 580° C. to 610° C., contact times in the range 20 ms to 500 ms, preferably in the range 50 ms to 200 ms (ms=millisecond), and solid flow rates in the range 150 to 600 kg/s/m².

The contact time is defined as the ratio of the volume of catalyst present in the reactor to the volumetric flow rate of fluid passing through the reactor under the operating conditions of the cracking reactor.

This set of conditions means that the secondary riser is operated at catalyst to feed ratios (denoted C/O) in the range 8 to 35, preferably in the range 10 to 25.

In the case of a principal downer, this operates with a catalyst to feed ratio in the range 5 to 40, and preferably in the range 10 to 30, and at downer outlet temperatures (denoted TO) in the range 500° C. to 650° C., preferably in the range 550° C. to 630° C.

The optimum conditions for propylene production in a secondary downer are obtained for outlet temperatures from said secondary downer in the range 550° C. to 650° C., preferably in the range 580° C. to 630° C., contact times in the range 20 ms to 800 ms, preferably in the range 50 ms to 500 ms (ms=millisecond). The present invention consists of recycling to the reaction section of a FCC unit a stream of principally olefinic C4, C5 and C6 compounds. This recycling stream is removed from the inter-stage of the wet gas compressor (denoted WGC).

The advantage of the present invention is withdrawal of this recycle not after the separation section but upstream thereof, which means that separation costs can be dispensed with and that it is possible to benefit from a recycle with properties (composition) as good as or even better than (lower quantity of aromatics) those of the gasoline recycle.

For simplification, this stream will hereinafter be termed the inter-stage stream. The stream deriving from the inter-stage of the wet gas compressor is broadly composed of C4 and C5 olefins, typically in a proportion in the range 30% to 80%.

These C4 and C5 compounds have high olefinicity, i.e. a high proportion of unsaturated compounds which may be as high as 50% to 80% by weight for the C4 cut, and 40% to 65% by weight for the C5 cut. These unsaturated compounds from the inter-stage stream are subjected to oligomerization reaction conditions under the particular operating conditions in a FCC riser leading to the production of compounds with a longer carbon chain. These oligomerized compounds then in turn undergo catalytic cracking reactions resulting in the formation of significant quantities of propylene.

The olefinic C4, C5 and C6 molecules contained in the inter-stage stream in question may be recycled either to the principal reactor or to the secondary reactor when the FCC unit already includes such a secondary reactor.

In the case of recycling to the principal reactor, this recycle may be carried out either directly as a mixture with the heavy feed or upstream of the injectors for said heavy feed via dedicated injectors or a pipe inside the riser.

In the case of recycling to the secondary riser, this may be either a dedicated riser, i.e. treating only the recycle in question, or a secondary riser already converting a light feed such as a portion of the gasoline produced in the principal riser, with a view to propylene production.

In order to guarantee a stable flow rate of the inter-stage stream to the principal or secondary riser (which may vary due to fluctuations in the operation of the unit and compressor), it is possible to associate with the inter-stage stream a makeup which may derive from the downstream portion of the gas plant, preferably a catalytic gasoline. This makeup may also be constituted by any liquid compound originating from oil or from biomass, preferably with an olefins content of more than 20% and a number of carbon atoms of less than 12, in order to increase the propylene production potential.

This makeup may be removed from the head of the FCC gasoline splitter, at the bottom of the depropanizer. It may also derives from an oligomerization unit or from a Pygas unit coming from a steam cracker.

DETAILED DESCRIPTION OF THE INVENTION

The following description is made with reference to FIG. 1.

FIG. 1 shows a catalytic cracking unit with two risers (FCC), a principal riser 1 and a secondary riser 2. The principal riser 1 is supplied with regenerated catalyst via a line 10 and the secondary riser is supplied with regenerated catalyst from a line 9. The regeneration zone has two stages, a first stage 4 and a second stage 3 connected to the first stage via a catalyst transfer line 6.

The catalyst is transferred to the regeneration zone, leaving the stripping zone 8 via a transfer line 5.

The principal riser 1 is supplied with a conventional feed (CH1) and the secondary riser 2 is supplied with a lighter feed denoted CH2.

The stream of effluents 11 leaving the FCC unit is introduced into the separation column MC from which an overhead stream denoted 12, one or more intermediate streams 14 and a bottom stream 13 are withdrawn. The intermediate streams 14 and the bottom stream 13 will not be described further because they are not pertinent to the present invention.

Thus, the description is taken up again at the overhead stream 12 which is condensed in the drum BS and separated into two phases:

the liquid phase, a portion of which supplies the column MC as a reflux, and another portion of which 25 supplies the separation located downstream of a wet gas compressor WGC which comprises two stages ET1, ET2;

the gas phase 15 derives from the drum BS and is directed towards the first stage of the gas compressor ET1 after having been freed of liquid particles which it may contain in the separator drum BS1.

The compressed stream 16 deriving from the first stage ET1 is directed to a second drum separator BS2 from which 3 streams are extracted:

a stream 19 which is directed towards the second compression stage ET2 after being passed into the separator drum BS3, thereby becoming the stream 19a, free of liquid particles. The stream 19a is compressed in the second compression stage ET2 to deliver the compressed stream 21 which rejoins the cracked gas recovery section SPG;

a stream 20 which is directed towards the waste water treatment section (not shown in FIG. 1);

a stream 22 which is recycled to the principal riser 1 or the secondary riser 2 or partially towards the principal riser via the stream 25 and partially towards the secondary riser via the stream 24 and which constitutes the inter-stage stream.

Since, as can clearly be seen in FIG. 1, this stream 22 is indeed removed between the two compression stages ET1 and ET2 of the gas compressor, it is denoted the inter-stage stream.

The invention may thus in a general manner be described as a process for the production of gasoline and the co-production of propylene using a catalytic cracking unit having at least one principal reactor operating in upflow mode (termed a riser) or in downflow mode (termed a downer), treating a conventional heavy feed, and in which the principal reactor also treats a feed mainly constituted by olefinic C4, C5 and C6 molecules introduced as a mixture with the heavy feed or upstream of said heavy feed, said olefinic feed being removed from the inter-stage of the wet gas compressor WGC forming part of the gas treatment section SPG associated with the FCC unit and constituting the inter-stage stream.

In a variation of the process for the production of gasoline and the co-production of propylene in accordance with the invention, the olefinic C4, C5 and C6 cut is introduced upstream of the principal feed via a pipe inside said principal riser opening 1 m to 0.5 m before the injectors for the principal feed.

In general, if the principal reactor functions in downflow mode (downer), it functions under the following operating conditions: reactor outlet temperature in the range 580° C. to 630° C. and C/O ratio in the range 15 to 40, preferably in the range 20 to 30, residence time in the range 0.1 to 1 s and preferably in the range 0.2 to 0.7 s.

In a variation of the process for the production of gasoline and for the co-production of propylene of the invention, said process employs a catalytic cracking unit having a principal riser 1 treating a conventional feed CH1 and a secondary riser 2 functioning in parallel with the principal riser 1 treating a feed CH2 which is lighter than the heavy feed CH1 and operating under more severe conditions than those of the principal riser, said secondary riser 2 treating the olefinic C4, C5, C6 cut, represented by the stream 22 deriving from the inter-stage of the wet gas compressor WGC.

In the same variation in which the process of the invention employs a catalytic cracking unit using a principal riser 1 and a secondary riser 2, said secondary riser may treat a mixture of the olefinic C4 C5 C6 cut (stream 22) deriving from the inter-stage of the wet gas compressor WGC, a recycled gasoline cut and/or an oligomerizate C5, C6, C7 or C8, not shown in FIG. 1.

In the same variation in which the process of the invention uses a catalytic cracking unit employing a principal riser 1 and a secondary riser 2, it is possible to add to the inter-stage stream a makeup stream 23 constituted by recycled gasoline in order to guarantee that the sum of the two streams, i.e. the inter-stage stream 22 plus the makeup stream 23, is constant to plus or minus 10%.

In the same variation in which the process of the invention uses a catalytic cracking unit employing a principal riser 1 and a secondary riser 2, the makeup stream 23 may be constituted by a hydrocarbon cut of oil or biomass origin, having an olefins content of more than 20% by weight and containing compounds containing less than 12 carbon atoms.

In the same variation in which the process of the invention uses a catalytic cracking unit employing a principal riser 1 and a secondary riser 2, the makeup stream 23 may be removed either from the head of the FCC gasoline splitter or from the bottom of the depropanizer forming part of the gas treatment section (gas plant).

In the same variation in which the process of the invention uses a catalytic cracking unit employing a principal riser 1 and a secondary riser 2, the makeup stream 23 may originate from an oligomerization or from pygas, from a steam cracker.

In a variation in which the process of the invention uses a catalytic cracking unit employing a principal riser 1 and a secondary riser 2, the secondary riser 2 functions with a contact time in the range 20 to 500 ms, preferably in the range 50 ms to 200 ms, and solid flow rates in the range 150 to 600 kg/s·m².

In the variation in which the process of the invention uses a catalytic cracking unit employing a principal riser 1 and a secondary riser 2, the C/O ratio of the principal riser is in the range 6 to 14, preferably in the range 7 to 12, and the C/O ratio of the secondary riser is in the range 8 to 35, preferably in the range 10 to 25.

In the variation in which the process of the invention uses a catalytic cracking unit employing a principal riser 1 and a secondary riser 2, the outlet temperature for the principal riser is in the range 510° C. to 580° C., preferably in the range 520° C. to 570° C., and the outlet temperature for the secondary riser is in the range 550° C. to 650° C., preferably in the range 580° C. to 610° C.

EXAMPLES

Five examples denoted 1, 2, 3, 4 and 5 will be used to illustrate the present invention.

Example 1

This first example constituted the basic case and corresponded to a mono-riser FCC unit with a capacity of 70000 BPSD, i.e. 500 m³/hour (BPSD is the abbreviation of barrels per day), treating a residue feed functioning under maxi-propylene conditions, i.e. with a catalytic system containing a form selective zeolite in order to improve the LPG-to-gasoline selectivity and operating under more severe operating conditions than standard maxi-gasoline conditions.

The principal characteristics of the feed as well as the operating conditions under consideration are respectively shown in Tables 1 and 2 below.

TABLE 1

| principal characteristics of heavy feed | | |
|---|---|---|
| 15/4 density, ° C. | | 0.9305 |
| Sulphur | wt % | 1.671 |
| Nitrogen | ppm by weight | 1222 |
| Conradson carbon residue | wt % | 4.36 |
| Nickel | ppm | 12 |
| Vanadium | ppm | 19 |
| Viscosity (@ 50° C.) | cSt | 84 |
| Hydrogen | wt % | 12.33 |

TABLE 2

| operating conditions for Example 1 | | |
|---|---|---|
| | | Example 1 |
| Unit capacity | barrel/day | 70000 |
| Feed flow rate | t/h | 431.6 |
| Pressure, riser outlet | bar g | 1.4 |
| Temperature, riser outlet | ° C. | 550 |
| Temperature, feed pre-heat | ° C. | 260 |
| Steam flow rate (MP) | tonne/h | 29.6 |
| Ratio of flow rate of catalyst to flow rate of feed, by weight | | 8 |

Under these conditions, the flow rates of the products leaving the unit are given in Table 3 below:

TABLE 3 flow rates of products for Example 1

| kg/h | Example 1: Basic case |
|---|---|
| Dry gases | 22446 |
| NH$_3$ | 43 |
| H$_2$S | 3913 |
| H$_2$ | 516 |
| C1 | 6020 |
| C2 | 4988 |
| C2= | 6966 |
| GPL | 133171 |
| C3 | 7568 |
| C3= | 46612 |
| C4 | 17243 |
| C4= | 61748 |
| LIQUID | 236543 |
| IP-160 | 113004 |
| 160-220 | 39302 |
| IP-220° C. | 152306 |
| 220-360 | 54653 |
| 360+ | 29584 |
| Coke | 37840 |
| TOTAL | 430000 |

Example 2

Example 2 corresponds to Example 1 with a recycle from the inter-stage flow to a location upstream of the principal feed.

The operating conditions for the riser were identical to those of Example 1. Under these conditions, the flow rate of the inter-stage stream corresponded to 45 tonnes per hour and its composition is provided in Table 4 below.

TABLE 4 composition of inter-stage stream, Example 2

| Composition of inter-stage stream wt % | |
|---|---|
| C3 total | 4 |
| C4 total | 20 |
| C5 total | 30 |
| C6-C8 | 46 |
| C3= in total C3 | 86 |
| C4= in total C4 | 60 |
| C5= in total C5 | 51 |
| Recycle flow rate, t/h | 45 |

The flow rates leaving the unit with a recycle are given and compared with those of the basic case in Table 5 below:

TABLE 5 comparison of Example 1 and Example 2

| kg/h | Example 1 Basic case | Example 2 Inter-stage stream co-processed upstream of heavy feed | delta % |
|---|---|---|---|
| Dry gases | 22446 | 23627 | 5.3 |
| NH$_3$ | 43 | 43 | 0.0 |
| H$_2$S | 3913 | 3913 | 0.0 |
| H$_2$ | 516 | 571 | 10.6 |
| C1 | 6020 | 6511 | 8.2 |
| C2 | 4988 | 5243 | 5.1 |
| C2= | 6966 | 7346 | 5.5 |
| GPL | 133171 | 134432 | 0.9 |
| C3 | 7568 | 7927 | 4.7 |
| C3= | 46612 | 48616 | 4.3 |
| C4 | 17243 | 17855 | 3.5 |
| C4= | 61748 | 60035 | -2.8 |
| LIQUID | 236543 | 233089 | -1.5 |
| IP-160 | 113004 | 107500 | -4.9 |
| 160-220 | 39302 | 40752 | 3.7 |
| IP-220° C. | 152306 | 148252 | -2.7 |
| 220-360 | 54653 | 55110 | 0.8 |
| 360+ | 29584 | 29727 | 0.5 |
| Coke | 37840 | 38852 | 2.7 |
| TOTAL | 430000 | 430000 | 0.0 |

Under these conditions, a comparison of Tables 3 and 5 shows that the propylene gain was over 4%, which is clearly highly significant at industrial flow rates.

A loss of C4 and C5 (through the IP-160° C. cut) was obviously observed, since these compounds had been recycled and cracked.

An increase in the dry gases and coke was also observed but remained within acceptable limits for the unit, especially from the point of view of thermal balance. The gain of ethylene, which was also an upgradeable product, increased very significantly, rising by more than 5%.

The recycle of the inter-stage stream 22 upstream of the principal feed CH1 thus fully fulfilled the objective of maximizing the production of propylene while dispensing with the costs of separation compared with a conventional recycle of catalytic gasoline.

Example 3

Example 3 is similar to Example 2 with the exception that this time, the inter-stage stream was recycled to a dedicated secondary riser 2 and cracked under optimized conditions, namely a riser outlet temperature of 590° C. and a contact time of 250 ms. The flow rates of the products obtained are shown in Table 6 and compared with those of Example 1.

TABLE 6 comparison of Example 1 and Example 3

| kg/h | Example 1 Basic case | Example 2 Inter-stage stream co-processed upstream of heavy feed | delta % |
|---|---|---|---|
| Dry gases | 22446 | 24133 | 7.5 |
| NH$_3$ | 43 | 43 | 0.0 |
| H$_2$S | 3913 | 3913 | 0.0 |
| H$_2$ | 516 | 594 | 15.2 |
| C1 | 6020 | 6721 | 11.7 |
| C2 | 4988 | 5352 | 7.3 |
| C2= | 6966 | 7509 | 7.8 |
| GPL | 133171 | 134973 | 1.4 |
| C3 | 7568 | 8080 | 6.8 |
| C3= | 46612 | 49475 | 6.1 |
| C4 | 17243 | 18117 | 5.1 |
| C4= | 61748 | 59301 | -4.0 |
| LIQUID | 236543 | 231609 | -2.1 |
| IP-160 | 113004 | 105141 | -7.0 |
| 160-220 | 39302 | 41373 | 5.3 |
| IP-220° C. | 152306 | 146514 | -3.8 |
| 220-360 | 54653 | 55306 | 1.2 |

TABLE 6-continued comparison of Example 1 and Example 3

| kg/h | Example 1 Basic case | Example 2 Inter-stage stream co-processed upstream of heavy feed | delta % |
|---|---|---|---|
| 360+ | 29584 | 29789 | 0.7 |
| Coke | 37840 | 39286 | 3.8 |
| TOTAL | 430000 | 430000 | 0.0 |

When the inter-stage stream was recycled to a dedicated riser 2 and subjected to optimized operating conditions, the propylene gain compared with the basic case (Example 1) was more than 6%. Thus, this is an improvement over the gain of 4% observed when that same recycle was cracked in the principal riser upstream of the heavy feed.

Under these conditions, the ethylene also increased more with a gain of almost 8% compared with 5% in Example 2.

The increase in dry gases and coke was higher than in Example 2, but this rise was still limited.

The recycle of the C4 and C5 rich cut in a dedicated riser thus means that higher propylene gains are possible compared with when that feed is cracked in a single riser upstream of the principal feed.

Example 4

The following example constitutes a second basic case and corresponds to a FCC unit comprising two risers, a principal riser 1 supplied with a residue feed CH1, the same as for example 1, and a secondary riser 2 in which a portion of the catalytic gasoline produced, CH2, is recycled and cracked under severe conditions. As was the case with example 1, the catalytic system comprised a zeolite with form selectivity in order to optimize the maxi-propylene operation of the unit.

The operating conditions of Example 4 are described in Table 7.

TABLE 7

Operating conditions for Example 4

| Case | | Example 4 |
|---|---|---|
| Unit capacity | barrel/day | 70000 |
| *Principal riser* | | |
| Residue feed flow rate | t/h | 431.6 |
| Pressure, riser outlet | bar g | 1.4 |
| Temperature, riser outlet | ° C. | 550 |
| Temperature, feed pre-heat | ° C. | 260 |
| Steam flow rate (MP) | t/h | 29.6 |
| Ratio of flow rate of catalyst to flow rate of feed, by weight | | 8 |
| *Secondary riser* | | |
| Catalytic gasoline recycle flow rate | t/h | 108 |
| Riser outlet temperature | ° C. | 590 |
| Recycle temperature | ° C. | 53 |
| Steam flow rate (MP) | t/h | 3.3 |
| Ratio of flow rate of catalyst to flow rate of feed, by weight | | 12 |

On this basis, the flow rates of the products leaving the unit are given in Table 8:

TABLE 8 flow rates of products for Example 4

| kg/h | Example 4 Basic dual riser case, gasoline recycle |
|---|---|
| Dry gases | 24940 |
| $NH_3$ | 43 |
| $H_2S$ | 3913 |
| $H_2$ | 602 |
| C1 | 7095 |
| C2 | 5504 |
| C2= | 7783 |
| GPL | 142115 |
| C3 | 8600 |
| C3= | 51600 |
| C4 | 18060 |
| C4= | 63855 |
| LIQUID | 224632 |
| IP-160 | 97782 |
| 160-220 | 41667 |
| 1P-220° C. | 139449 |
| 220-360 | 55556 |
| 360+ | 29627 |
| Coke | 38313 |
| TOTAL | 430000 |

Example 5

Example 5 is similar to Example 4, but this time with a recycle of the inter-stage stream to the secondary riser mixed with gasoline from the FCC unit. Compared with Example 2, this recycle was changed in composition but the same recycle flow rate was assumed.

The composition of this recycle is shown in Table 9.

TABLE 9 composition of inter-stage stream, Example 5

| Composition of inter-stage stream wt % | |
|---|---|
| C3 total | 6 |
| C4 total | 20 |
| C5 total | 56 |
| C6-C8 | 18 |
| C3= in total C3 | 84 |
| C4= in total C4 | 80 |
| C5= in total C5 | 51 |
| Recycle flow rate, t/h | 45 |

The flow rates leaving the unit with a recycle are given and compared with those of Example 4 in Table 10 below:

TABLE 10 comparison of Example 4 and Example 5

| kg/h | Example 4 Basic dual riser case, gasoline recycle | Example 5 Dual riser, recycle of gasoline, ET inter-stage flow, to secondary riser | delta % |
|---|---|---|---|
| Dry gases | 24940 | 26911 | 7.9 |
| $NH_3$ | 43 | 43 | 0.0 |
| $H_2S$ | 3913 | 3913 | 0.0 |
| $H_2$ | 602 | 713 | 18.4 |
| C1 | 7095 | 7921 | 11.6 |
| C2 | 5504 | 5995 | 8.9 |
| C2= | 7783 | 8326 | 7.0 |
| GPL | 142115 | 142487 | 0.3 |
| C3 | 8600 | 9119 | 6.0 |
| C3= | 51600 | 54550 | 5.7 |

TABLE 10-continued comparison of Example 4 and Example 5

| kg/h | Example 4 Basic dual riser case, gasoline recycle | Example 5 Dual riser, recycle of gasoline, ET inter-stage flow, to secondary riser | delta % |
|---|---|---|---|
| C4 | 18060 | 18828 | 4.3 |
| C4= | 63855 | 59989 | −6.1 |
| LIQUID | 224632 | 220888 | −1.7 |
| IP-160 | 97782 | 92349 | −5.6 |
| 160-220 | 41667 | 42873 | 2.9 |
| IP-220° C. | 139449 | 135222 | −3.0 |
| 220-360 | 55556 | 55959 | 0.7 |
| 360+ | 29627 | 29707 | 0.3 |
| Coke | 38313 | 39714 | 3.7 |
| TOTAL | 430000 | 430000 | 0.0 |

The recycle of the inter-stage stream mixed with gasoline from the FCC unit can substantially increase the propylene yield, with a rise of almost 6%.

The ethylene increased significantly with a gain of 7%. The coke and dry gas yields increased but remained within acceptable limits.

The ethylene increased by 7%, the dry gases by almost 8% and coke by less than 4%.

These examples show that in all of the gases, a recycle of the inter-stage stream 22 either to the principal riser 1 or to the secondary riser 2 or partly to the principal riser 1 and partly to the secondary riser 2 can very significantly increase the propylene yield.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application Ser. No. 10/01955, filed May 6, 2010, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the production of gasoline and the co-production of propylene comprising cracking a principal feed that is a conventional heavy feed (CH1) in a catalytic cracking unit having at least one principal reactor (1) functioning in upflow mode or downflow mode and optionally treating a lighter feed (CH2) in a secondary riser (2) functioning under more severe conditions than the principal riser (1) and treating an olefinic feed constituted mainly by C4, C5 and C6 olefinic molecules in addition to principal feed (CH1) and optional feed (CH2), after removing said olefinic feed as inter-stage stream (22) from an inter-stage of a wet gas compressor forming part of a gas treatment section (SPG) associated with the catalytic cracking unit.

2. A process for the production of gasoline and the co-production of propylene according to claim 1, comprising introducing the olefinic C4, C5 and C6 feed corresponding to the inter-stage stream (22) as a mixture with the heavy feed (CH1) when the catalytic cracking unit has only one principal reactor (1).

3. A process for the production of gasoline and the co-production of propylene according to claim 1, comprising introducing the olefinic C4, C5 and C6 feed corresponding to the inter-stage stream (22) upstream of the principal feed (CH1) via a pipe inside said principal riser (1) opening 1 m to 0.5 m before the level of injectors for the principal feed (CH1), when the catalytic cracking unit has only one principal reactor (1).

4. A process for the production of gasoline and the co-production of propylene according to claim 1, comprising introducing the olefinic C4, C5 and C6 cut corresponding to the inter-stage stream (22) into the secondary riser (2) when the catalytic cracking unit further has a secondary riser (2) treating a lighter feed (CH2), and working under more severe operating conditions than those of the principal riser.

5. A process for the production of gasoline and the co-production of propylene according to claim 4, comprising treating the olefinic C4 C5 C6 cut corresponding to the inter-stage stream (22) and a recycled gasoline cut and/or a C5, C6, C7 or C8 oligomerizate cut as a mixture said secondary riser (2).

6. A process for the production of gasoline and the co-production of propylene according to claim 1, further comprising adding a makeup stream (23) containing recycled gasoline to the inter-stage stream (22) in order to ensure that the sum of the inter-stage stream (22) plus the makeup stream (23), is constant to plus or minus 10%.

7. A process for the production of gasoline and the co-production of propylene according to claim 6, in which the makeup stream (23) comprises a hydrocarbon cut of oil or biomass origin having an olefins content of more than 20% by weight and containing compounds having less than 12 carbon atoms.

8. A process for the production of gasoline and the co-production of propylene according to claim 6, in which the makeup stream (23) is removed either from the head of a gasoline splitter or from the bottom of a depropanizer forming part of the gas treatment section (SPG).

9. A process for the production of gasoline and the co-production of propylene according to claim 6, in which the makeup stream (23) derives from an oligomerization unit or from pygas, from a steam cracker.

10. A process for the production of gasoline and the co-production of propylene according to claim 4, in which contact time in the secondary riser (2) is in the range 20 to 500 ms, and solid flow rates are in the range 150 to 600 kg/s·m².

11. A process for the production of gasoline and the co-production of propylene according to claim 4, in the principal riser (1) has a C/O ratio in the range 6 to 14, and the secondary riser (2) has a C/O ratio in the range 8 to 35.

12. A process for the production of gasoline and the co-production of propylene according to claim 4, in which the outlet temperature from the principal riser (1) is in the range 510° C. to 580° C., and the outlet temperature from the secondary riser (2) is in the range 550° C. to 650° C.

* * * * *